(12) United States Patent
Jensen

(10) Patent No.: US 6,360,620 B1
(45) Date of Patent: Mar. 26, 2002

(54) METHOD AND SAMPLE EXTRACTOR FOR THE EXTRACTION OF INTACT FLUID SAMPLES

(75) Inventor: Hans Christian Jensen, Hemmet (DK)

(73) Assignee: Rotek A/S, Tarm (DK)

(*) Notice: Subject to any disclaimer, the term of this patent is extended or adjusted under 35 U.S.C. 154(b) by 0 days.

(21) Appl. No.: 09/147,825

(22) PCT Filed: Sep. 16, 1997

(86) PCT No.: PCT/DK97/00390

§ 371 Date: Mar. 15, 1999

§ 102(e) Date: Mar. 15, 1999

(87) PCT Pub. No.: WO98/12531

PCT Pub. Date: Mar. 26, 1998

(30) Foreign Application Priority Data

Sep. 16, 1996 (DK) .............................................. 0997/96

(51) Int. Cl.[7] .............................. G01N 1/12; E21B 49/08
(52) U.S. Cl. ................................ 73/864.62; 73/864.52; 73/864.63; 166/264
(58) Field of Search ........................ 73/864.62, 864.63, 73/864.64, 864.52; 166/264

(56) References Cited

U.S. PATENT DOCUMENTS

| 4,372,382 A | * | 2/1983 | Rooney et al. ............. 166/264 |
| 4,461,186 A | | 7/1984 | Brännström et al. ..... 73/864.62 |
| 4,660,423 A | | 4/1987 | Armstrong et al. ...... 73/864.52 |
| RE34,754 E | * | 10/1994 | Dickinson et al. ... 73/864.34 X |
| 5,377,755 A | * | 1/1995 | Michaels et al. ........... 166/264 |
| 5,775,424 A | * | 7/1998 | Pemberton et al. ......... 166/264 |
| 5,804,743 A | * | 9/1998 | Vroblesky et al. ... 73/864.51 X |
| 6,148,914 A | * | 11/2000 | Guieze ................ 73/864.62 X |

FOREIGN PATENT DOCUMENTS

| DE | 34 44 363 | | 6/1986 |
| DE | 19530709 A1 | * | 2/1996 |
| DE | 195 30 709 C2 | | 2/1996 |

* cited by examiner

Primary Examiner—Thomas P. Noland
(74) Attorney, Agent, or Firm—Nixon Peabody LLP; David S. Safran

(57) ABSTRACT

The extraction of intact, representative fluid samples in well-defined depths, such as from wells sunk into the ground, has until now been very difficult, and in many cases impossible to perform. A method is provided as well as a sample extractor for the extraction of intact fluid samples, in particular from a well (26) sunk into the ground, by submersion of a compressible hollow flexible body (22) fitted in a supporting device which, subsequent to submersion to the sample extraction depth, is acted upon to effect liquid entry through an inlet. In particular, hollow flexible body (22) is held in the support device in the form of a pressure vessel (2) and fully compressed by pressurized gas inside the pressure vessel, whereupon the pressure vessel is caused to change in such a way that a surrounding fluid seeps into the hollow flexible body (22), whereupon the vessel (2) with the body (22) containing the fluid sample is hoisted out of the well (26).

18 Claims, 3 Drawing Sheets

METHOD AND SAMPLE EXTRACTOR FOR THE EXTRACTION OF INTACT FLUID SAMPLES

BACKGROUND OF THE INVENTION

1. Field of the Invention

The invention relates to a method for the extraction of intact liquid samples, in particular, from a well sunk into the ground, by submersion of a compressible hollow flexible body fitted in supporting means which, subsequent to submersion to the sample extraction depth, is acted upon to effect liquid entry through an inlet, as well as a sample extractor for performing the method.

2. Description of Related Art

Such a sample extractor is known from U.S. Pat. No. 4,461,186 which comprises a sterile flexible body in the form of a tubular bag, the openings of which are fitted by means of compression rings to two rigid endpieces, the upper of which comprising an inlet being releasably fitted to the console of a sample extractor, and the lower being fitted in the vertically displaceable console of the sample extractor which is forced away from the upper endpiece by elastic means. The lower endpiece comprises a vertical pin projecting up into the bag volume and fitting into said inlet in such a manner that the endpieces are placed at a certain distance from another in the starting position, corresponding to the length of the pin, whereby air will be present in the bag at the commencement of sample extraction.

The inlet in the upper endpiece is covered by a hose which is connected to a glass tube fixed in a crunching mechanism. The sample extraction is activated in that a weight is dropped when the sample extracted with a bag fitted is placed at the desired depth, said weight falling on the crunching mechanism which fractures the glass tube whereby the inlet opening is uncovered, and liquid may flow through it. The same mechanism is further connected to a release mechanism which releases the lower endpiece so that this, due to the influence of the downward directed elastic means, is displaced such that sample material is sucked through the inlet in the upper endpiece. The sample extraction is terminated in that the lower endpiece acts on a spring loaded valve via a rod-and-spring which blocks the inlet in the upper endpiece. Subsequently the sample extractor is hoisted up and the fluid sample collected in the bag volume may be removed from the sample extractor along with the endpieces. The sample extraction hence occurs using the bellows principle, where an elastic influence on one endpiece away from the upper, fixed endpiece causes surrounding fluid to be sucked into the bag volume.

This known sample extractor would be adapted to use in extraction of samples in predetermined depths where the requirements for the method used are not particularly rigid, i.e., where it is known beforehand that the subsequent results of analyses are reasonably removed from the detection limit of the substances in question. Examples might be the extraction of water samples in marine areas in the sea or in lakes, and in wells and large-diameter wells, where sufficient room is available for the submersion of the complete sample extraction equipment.

The extraction of fluid or water samples in order to detect substances endangering the environment in the course of evaluation of, e.g., the extent and distribution of ground water pollution is commonly performed. The extraction of the water samples directly at the filter of a well as well as in the water claiming area, where the water samples are extracted in pipes placed in the ground for this purpose.

Since the concentrations of the substances endangering the environment in, e.g., drinking water wells and water claiming areas are often near the detection limit, it is of a large importance that the samples are extracted in such a way that it is representative of the actual water quality in a given level at the particular sample extraction site.

Hence rigid requirements are put on the cleanliness of the equipment used for the sample extraction, while it is of a large importance that the samples may be extracted in different depths in the well, such that these are representative, and to enable the extraction of samples which are non-oxidised and which have not been subjected to atmospheric air, whereby gasses which may have been dissolved in the water sample might escape.

It would be impossible to use the sample extractor described in U.S. Pat. No. 4,461,186 for the extraction of the mentioned intact liquid samples which have to be analysed for substances occurring in concentrations very close to the detection limit. There are several reasons for this, e.g., atmospheric air will be present in the bag volume at commencement of the sample extraction. Lowering of the sampling equipment will cause turbulence and mixing of layers possibly occurring within the well, due to the construction and size of the equipment. This situation is further aggravated by dropping weight in order to crunch the glass tube which initiates the sample extraction.

Alternatively intact water samples may be extracted by means of a vacuum pump situated on the ground by the well, which sucks the water sample into a sample bottle. However, it may be difficult to determine the precise depth from which the sample is pumped, and there may be doubts as to possible contamination by substances present in the higher water layers in the well. Furthermore, there remains the fact that the pumped water sample cannot avoid, however briefly, to be in contact with air when it is fed to a sample container, which is undesired as described above. The problem with using a vacuum pump is furthermore that it hardly functions at depths exceeding 10 m. However, in order to solve this problem, pumps are known which are so small that they may be sunk into the well and pump the samples up. If such a pump is to be used in other locations, it must be cleaned first which is a time consuming and hence cost creating work which sometimes makes one use one pump per well which is costly in acquisition but often necessary, but even here remains the problem of the sample's contact with air.

SUMMARY OF THE INVENTION

It is the purpose of the present invention to provide a method for the extraction of intact fluid samples, in particular from a well sunk into the ground, by submersion of a compressible hollow flexible body fitted in supporting means comprising an inlet which, subsequent to submersion to the sample extraction depth, is filled with fluid, and a sample extractor to perform the method which alleviates the disadvantages concerning the use of the known pumps and which permits the extraction of intact and representative water samples without allowing the extracted samples to contact the atmosphere during sample extraction.

It has been realised in the invention that this purpose is obtainable in that the hollow flexible body is held in support means in the form of a pressure vessel during lowering to the desired sample extraction depth and filly compressed by means of a pressurised gas inside the pressure vessel, whereupon the pressure in the pressure vessel is caused to change in such a way that a surrounding fluid seeps into the hollow flexible body.

Due to the fact that the hollow flexible body is fully compressed until the seeping of the fluid is effected by releasing the pressure in the pressure vessel it is obtained that the collected fluid sample does not contact the atmosphere which means that the sample remains intact and hence un-influenced, until it is analysed.

For the performance of the methods, a sample extractor is provided of the kind in which the support means are constituted by a leak-proof container in which is placed the compressible hollow flexible body in the form of a bag of a suitable clean and resistant material, the open end of which is connected to the inlet in an air- and fluid tight manner, and which container is connected to a hose, at the other end of which means are provided for controlling the pressure between the wall of the container and the outside of the bag, which inlet is preferably provided at a bottom end of the container, viz. a removable tightly fitting plug, to which is fitted the flexible body and which has a through passage with an embedded one-way valve.

It is hereby possible to lower the sample extractor to the preferred depth in, e.g., a well, and here extract an intact fluid sample by equalising the pressure in the pressure vessel at the valve, whereby the surrounding liquid pressure in the well will cause a flow of liquid through the one-way valve and into the bag.

In order to avoid the collection of liquid in the gap of the one-way valve at the valve seat during the lowering of the sample extractor to the desired sample extraction depth, the one-way valve seat is oblong and conical, and the plunger is similarly inverse oblong and fitting to the valve seat, and the valve seat furthermore communicates with a preferably oblique passage in the longitudinal direction in the lower end of the plug, so that the lower part of the oblong conical plunger projects into the passage.

The functioning of this embodiment of the one-way valve and the plug is that there is no cavity in the opening of the one-way valve in which liquid may collect, because the plunger fills the opening of the one-way valve completely. Furthermore the embodiment of the one-way valve ensures a very large sealing surface between the valve seat and the plunger. Furthermore the oblique disposition of the passage contributes to ensuring that the liquid collected in the bag via the one-way valve is representative for the level below the surface of the liquid to which the sample extractor has been lowered, as during the lowering below the water table there will be a flow of liquid through the passage, and hence the liquid present in the passage will always come from the liquid present at the level to which the sample extractor has been lowered.

In order to prevent the influence of liquid pressure on the plunger of the one-way valve, the lower part of the plug may be of a conical shape, hereby the passage is protected and also the end of the plunger projecting into it, however without blocking the passage.

In order to ensure that there is no air in the bag during the lowering of the sample extractor and during the sample extraction, the upper part of the plunger of the one-way valve, around which the bag is fitted may be rounded and mutually adjusted in such a way that there are no air pockets present between the mouth of the bag and the top of the plug and said plunger in the compressed condition of the bag during lowering for the extraction of a liquid sample and such that turbulent liquid flow via the one-way valve into the volume of the bag is prevented.

In order to remove minute undesired amounts of air between the water level in the liquid sample collected in the bag and the top of the bag, the bag may be fitted with a valve at its closed end for the expulsion of air before packing and sending the sample for analysis.

In order to enable the control of the pressure of the fluid which compresses the body in the sample extractor, the pressure hose between the container and the valve may be fitted with a double tee fitted with a pressure indicator, a one-way valve with a fitting for connecting to a pressure source.

In order to enable the use of the sample extractor for the extraction of samples at small distances below a water table, the double tee may be connected to a valve for the control of pressure, a pressure indicator and the double tee may optionally be connected via a valve to a source of pressure and/or vacuum, whereby the pressure chamber may respectively be supplied with pressure for complete compression of the bag during lowering and vacuum during the actual sample extraction, whereby liquid is sucked into the bag.

It should be mentioned that the method according to the invention as well as the sample extractor for performing the method may also be used for sample extraction in other connections than for the extraction of samples in a well sunk into the ground. The invention is furthermore suitable for the extraction of intact samples in, e.g., lakes, open wells, tanks, including oil separators.

The invention is explained in greater detail in the following with reference to the accompanying drawings.

DETAILED DESCRIPTION OF THE INVENTION

Figure 1:
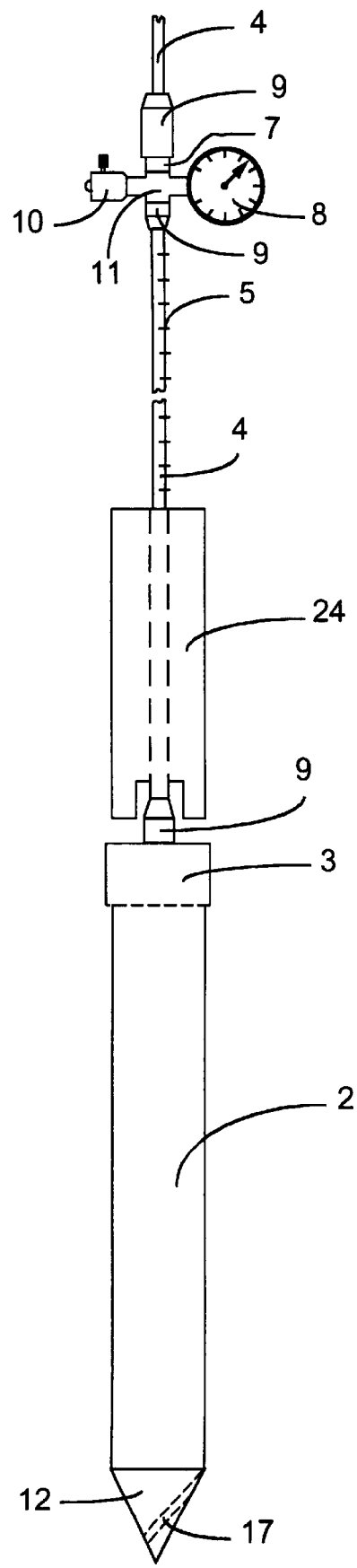
FIG. 1 is a side view of a sample extractor according to the invention.
Figure 2:
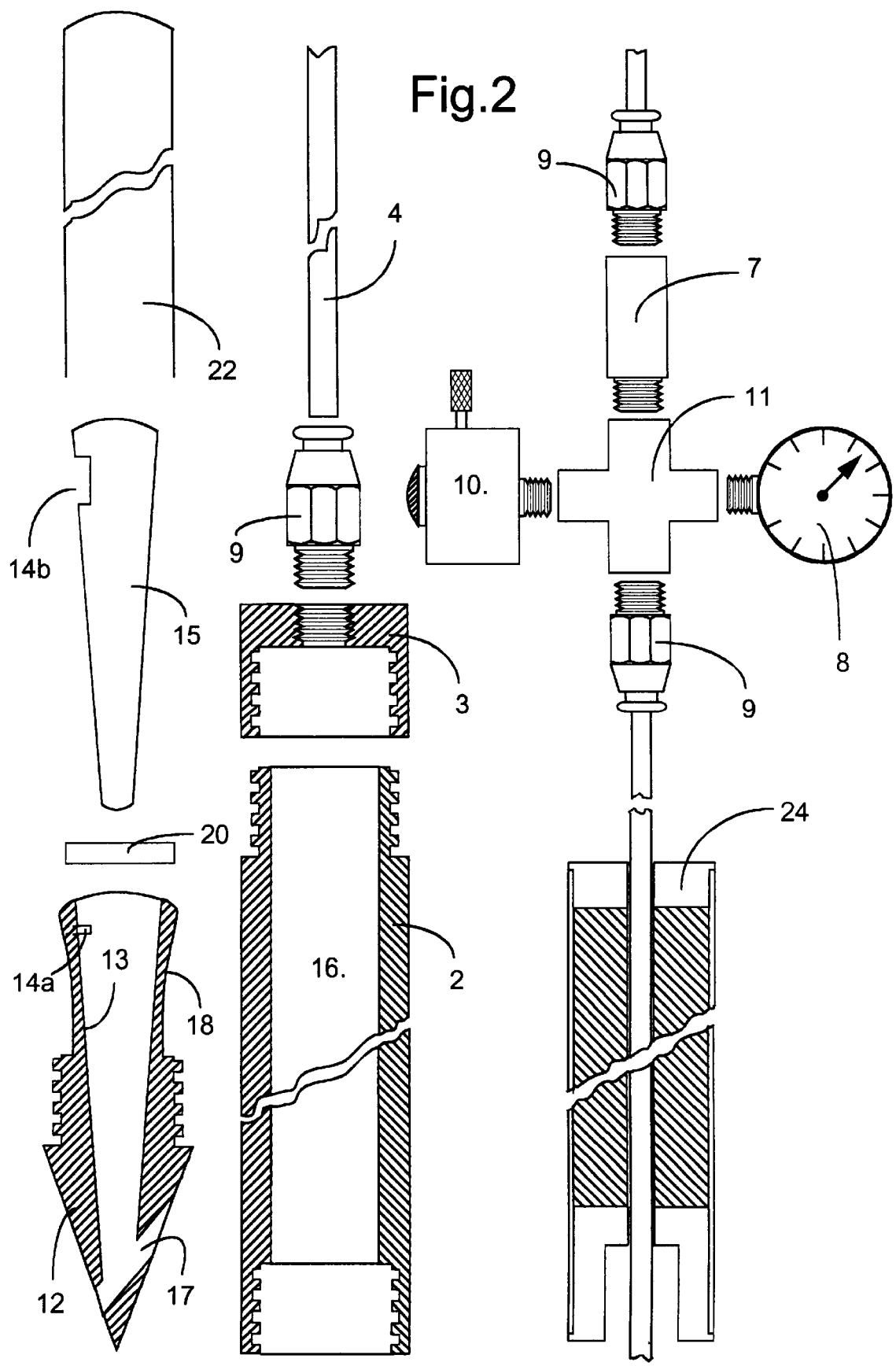
FIG. 2 is an exploded detailed side view of a sample extractor according to the invention.

The sample extractor shown in FIGS. 1 and 2 comprises a sealed container 2 in the upper end of which there is a sealed threaded plug 3 with a quick-release connector 9 in which there is connected a pressure hose 4 supplied with distance markings 5 in its longitudinal direction. The pressure hose 4 is connected via a quick release connector 9 at the end opposite the container to a double tee 11 supplied with a valve or a one-way valve which via a quick-release connector 9 is connected to not shown source of pressure or vacuum. A pressure indicator is furthermore connected to the double tee which, in the embodiment shown, is a manometer 8, and a blower valve 10.

The lower end of the container is supplied with a screwed-in sealed plug 12, the lower end of which is oblong conical, and in the central part of which there is a one-way valve consisting of an oblong conical valve seat 13 and a plunger 15 co-operating therewith, the movements of which are checked by a pin 14a projecting into a recess 14b in the plunger 15 in order that flow into the space 16 of the container only is permitted.

The bottom part of the plug has a crosswise and obliquely upwards directed passage 17 which communicates with the lower end of the valve seat, so that the plunger 15 of the one-way valve projects into the passage 17 without blocking it. The upper part of the plug has a stud 18 upon which a bag 22 in a suitable, sterile and resistant material has been fixed by fixation means 20 so that liquid flowing through the one-way valve is led to the inside of the bag. At the upper part of the container 2 there is fitted a weight 24 for overcoming the buoyancy of the container when it is lowered below a liquid surface.

The upper part of the plug 12 is rounded at the edge and made to fit a rounded shape on the plunger of the one-way valve 15. The purpose of this is partly to avoid sharp voids in which air pockets may collect between the compressed bag 22 and the parts mentioned and partly to counteract turbulent liquid flow during the sample extraction.

Before sample extraction by means of the sample extractor, it is prepared in order to compress the bag 22 completely inside the container 2, which is performed in that a fluid (e.g., atmospheric air) is supplied under pressure by means of the air valve to the container volume 16. The compressed air may be supplied to the container volume, e.g., by means of a well-known bicycle pump via the pressure hose 4 and the one-way valve 7 on the double tee 11.

Figure 3:
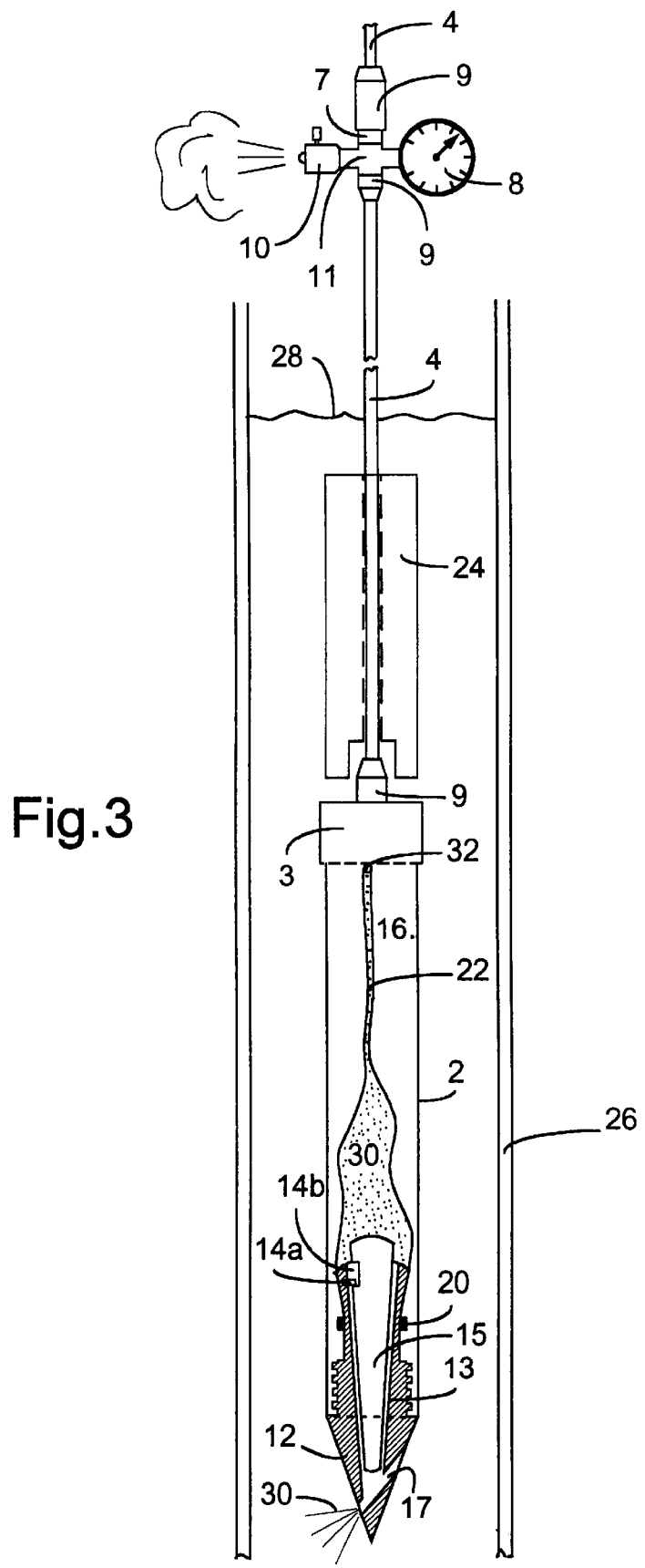
FIG. 3 is a side section of the same lowered into a well during sample extraction.

FIG. 3 shows the sample extractor during the taking of a sample in a well 26. It is presupposed that the sample extractor has been lowered to the preferred sampling depth, below the water level 28 in the well 26 which may be easily determined by means of the distance markings 5 on the pressure hose 4. The liquid sample is now obtained by opening the aeration valve 10, whereby the pressure in the pressure hose 4 and hence also in the volume 16 of the container are equalised, and hence also the pressure which compresses the bag 22. The external liquid pressure on the container and the opening of the one-way valve will cause the liquid 30 to flow through the opening of the one-way valve into the bag 22 in accordance with the equalisation of the pressure in the container, as indicated in FIG. 3.

When the pressure in the container 2 has been completely equalised the bag 22 is completely filled with liquid 30. The sample extractor is subsequently hoisted out of the well 26 and the liquid 30 collected in the bag is retained by means of the plunger 15 of the one-way valve which blocks the connection to the passage 17. The bag 22 containing the liquid 30 may be carefully removed from the bottom of the container 2 together with the plug 12, by loosening the latter, so that the extracted liquid sample does not get in contact with the surrounding air. The bag 22 with the plug 12 may subsequently be taken to a laboratory for analysis, alternatively be closed by means of squeezing below the plug 12, and the bag containing the liquid sample may be taken to a laboratory.

The bag may in a particular embodiment be fitted with a valve 32 at its closed end, via which certain minimal amounts of air between the inside of the bag 22 and the liquid sample may be removed, in case such amounts, against expectations were present during the removal of the bag with the liquid sample from the container 2.

The container 2 as well as the bag 22, the one-way valve 14, and the air hose are considered to be manufactured in a suitable resistant plastic material which is not dissolved or attacked by aggressive liquids. Furthermore the weight 24 considered to be coated with a similar material. As a particularly suitable material for the manufacture of the bag 22, it may be stated that this may advantageously be made of a Teflon film.

What is claimed is:

1. A method for the extraction of intact liquid samples by submersion of a compressible hollow flexible body which is fitted in a pressure vessel having a one-way valve in a lower part thereof and which, subsequent to submersion to a sample extraction depth, is acted upon to effect liquid entry through an inlet of said hollow flexible body, comprising the steps of:
   lowering the vessel with the hollow flexible body to a desired sample extraction depth, the hollow flexible body being fully compressed by means of a pressurized gas inside the pressure vessel and with surrounding liquid passing through and out of an inlet passage of said pressure vessel as it is lowered without admitting said liquid into the inlet of the hollow flexible body during said lowering;
   changing the pressure in the pressure vessel in such a way that a liquid sample is extracted from the surrounding liquid by the liquid seeping through said one-way valve and into the hollow flexible body; and
   after completion of sample extraction, hoisting the pressure vessel with said one-way valve blocking contact between the extracted liquid sample and matters outside the vessel to retrieve the sample extracted.

2. A sample extractor comprising:
   a leak-proof container having an openable passage for liquid;
   a compressible hollow flexible body in the form of a bag of a clean and resistant material fitted in said leak-proof container with an open end of the bag connected to said openable passage in an air- and fluid-tight manner; and
   a hose, one end of which is connected to said container and an opposite end of which is connected to a means for controlling the pressure between the container and an outer side of the bag;
   wherein said openable passage is formed in a plug that is removably tightly fitted to the open end of the bag, and wherein a one-way valve is provided in said plug for enabling liquid flow into said bag and for blocking liquid flow out of said bag.

3. A sample extractor according to claim 2, wherein said passage extends through said plug for enabling surrounding liquid to pass through and out of the passage without admitting said liquid into the hollow flexible body, and wherein said one-way valve intersects said passage without blocking it.

4. A sample extractor according to claim 2, wherein the one-way valve has an oblong conical valve seat and a similarly oblong conical the valve seat matching the valve seat, said valve seat being disposed in the plug in such a manner that the valve seat communicates with said passage; wherein said passage is longitudinally obliquely oriented in a lower end of the plug; and wherein a lower part of the oblong conical plunger projects into the passage.

5. A sample extractor according to claim 4, wherein the lower part of the plug has a conical shape.

6. A sample extractor according to claim 5, wherein an upper end of the plug and an upper end of the plunger, around which the bag is fixed, are rounded and matched such that no air pockets occur between mouth of the bag and the upper end of the plug and said plunger in the bag's compressed condition during lowering for the extraction of a liquid sample, and such that turbulent liquid flow through the one-way valve into the cavity of the bag is avoided.

7. A sample extractor according to claim 6, wherein the bag is supplied with a valve at a closed end, which enables the removal of undesired air between a surface of the liquid collected in the bag and a top of the bag immediately subsequent to the sample extraction and prior to packing for sending.

8. A sample extractor according to claim 7, wherein the means for controlling the pressure between the container and the outside of the bag comprises a double-tee to which is connected a pressure indicator and a one-way valve with an adaptor for connection to a source of pressure.

9. A sample extractor according to claim 7, wherein the means for controlling the pressure between the container and the outside of the bag during use of the sample extractor for taking samples at low depths below a liquid surface comprises a double-tee connected to a valve, a pressure indicator, and an adaptor connected to a source of pressure or vacuum.

10. A sample extractor according to claim 9, wherein a rate of change of pressure in the container is controlled by the valve connected to the double-tee, and hence also the velocity of the flow through the one-way valve in the plug into the bag.

11. A sample extractor according to claim 10, wherein a weight is fitted on top of the container in order to counter-act its buoyancy so that the container, and consequently the sample extractor, may be brought to a desired sampling depth below a liquid surface.

12. A sample extractor according to claim 2, wherein a lower part of the plug has a conical shape.

13. A sample extractor according to claim 2, wherein an upper end of the plug and an upper end of a plunger, around which the bag is fixed, are rounded and matched such that no air pockets occur between a mouth of the bag and the upper end of the plug and said plunger in the bag's compressed condition during lowering for the extraction of a liquid sample, and such that turbulent liquid flow through the one-way valve into the cavity of the bag is avoided.

14. A sample extractor according to claim 2, wherein the bag is supplied with a valve at a closed end, which enables the removal of undesired air between the surface of the liquid collected in the bag and the top of the bag immediately subsequent to the sample extraction and prior to packing for sending.

15. A sample extractor according to claim 2, wherein the means for controlling the pressure between the container and the outside of the bag comprises a double-tee to which a pressure indicator and a one-way valve with an adaptor for connection to a source of pressure are connected.

16. A sample extractor according to claim 2, wherein that the means for controlling the pressure between the container and the outside of the bag during the use of the sample extractor for taking samples at low depths below a liquid surface comprises a double-tee connected to a valve, a pressure indicator, and an adaptor connected to a source of pressure or vacuum.

17. A sample extractor according to claim 2, wherein a rate of change of pressure in a pressure vessel is controlled by a valve, and hence also the velocity of the flow through the one-way valve in the plug into the bag.

18. A sample extractor according to claim 2, wherein a weight is fitted on top of the container in order to counter-act its buoyancy so that the container and consequently the sample extractor may be brought to the desired sampling depth below a liquid surface.

* * * * *